United States Patent
Nassar

(10) Patent No.: US 10,105,681 B2
(45) Date of Patent: Oct. 23, 2018

(54) METHODS AND MATERIALS FOR MICROORGANISM CAPTURE

(71) Applicant: RAN Biotechnologies, Inc., Beverly, MA (US)

(72) Inventor: Roger A. Nassar, Swampscott, MA (US)

(73) Assignee: Ran Biotechnologies, Inc., Beverly, MA (US)

( * ) Notice: Subject to any disclaimer, the term of this patent is extended or adjusted under 35 U.S.C. 154(b) by 0 days.

(21) Appl. No.: 14/773,024

(22) PCT Filed: Mar. 13, 2014

(86) PCT No.: PCT/US2014/026540
§ 371 (c)(1),
(2) Date: Sep. 4, 2015

(87) PCT Pub. No.: WO2014/151836
PCT Pub. Date: Sep. 25, 2014

(65) Prior Publication Data
US 2016/0008788 A1  Jan. 14, 2016

Related U.S. Application Data

(60) Provisional application No. 61/784,432, filed on Mar. 14, 2013.

(51) Int. Cl.

| | |
|---|---|
| *C07K 1/22* | (2006.01) |
| *C12N 7/02* | (2006.01) |
| *B01J 20/24* | (2006.01) |
| *C12N 11/10* | (2006.01) |
| *A61M 1/36* | (2006.01) |
| *C12N 11/02* | (2006.01) |
| *C12N 11/06* | (2006.01) |
| *C12N 11/08* | (2006.01) |
| *C12N 11/14* | (2006.01) |
| *B01J 20/26* | (2006.01) |
| *C12N 7/00* | (2006.01) |
| *C02F 3/10* | (2006.01) |

(52) U.S. Cl.
CPC .............. *B01J 20/24* (2013.01); *A61M 1/36* (2013.01); *B01J 20/265* (2013.01); *C07K 1/22* (2013.01); *C12N 7/00* (2013.01); *C12N 11/02* (2013.01); *C12N 11/06* (2013.01); *C12N 11/08* (2013.01); *C12N 11/10* (2013.01); *C12N 11/14* (2013.01); *C02F 3/108* (2013.01); *C12N 2760/16111* (2013.01); *C12N 2760/16151* (2013.01); *Y02W 10/15* (2015.05)

(58) Field of Classification Search
None
See application file for complete search history.

(56) References Cited

U.S. PATENT DOCUMENTS

| | | |
|---|---|---|
| 5,612,043 A | 3/1997 | Deprez et al. |
| 6,638,749 B1 | 10/2003 | Beckman et al. |
| 2006/0002852 A1* | 1/2006 | Saltzman ............. A61K 9/0019 424/1.11 |
| 2006/0292555 A1 | 12/2006 | Xu et al. |
| 2007/0141727 A1 | 6/2007 | Huang et al. |
| 2008/0070274 A1 | 3/2008 | Lee et al. |
| 2010/0015633 A1 | 1/2010 | Lu et al. |
| 2010/0075314 A1 | 3/2010 | Garimella et al. |
| 2010/0105112 A1 | 4/2010 | Holtze et al. |
| 2011/0027854 A1 | 2/2011 | Suda et al. |
| 2011/0117596 A1 | 5/2011 | Mattiasson et al. |
| 2012/0018382 A1 | 1/2012 | Stein |
| 2012/0040905 A1 | 2/2012 | Perret et al. |

FOREIGN PATENT DOCUMENTS

| | | |
|---|---|---|
| CN | 1243444 A | 2/2002 |
| EP | 0073611 A1 | 3/1983 |
| EP | 0230768 A1 | 8/1987 |
| WO | 9831383 A1 | 7/1998 |
| WO | 2007095279 A2 | 8/2007 |
| WO | 2014151836 A1 | 9/2014 |

OTHER PUBLICATIONS

Rusnati et al., The Journal of Biological Chemistry, 1997, 272(17):11313-11320.*
Non-final office action dated Nov. 8, 2016 in U.S. Appl. No. 14/773,059.
Medintz et al., Proteolytic activity monitored by fluorescence resonance energy transfer through quantum-dot-peptide conjugates, Nature Materials 2006 5:581-589.
Nassar et al., Removing human immunodeficiency virus (HIV) from human blood using immobilized heparin, Biotechnology Letters 2012 34(5):853-856.
Pissuwan et al., Prospects for gold nanorod particles in diagnostic and therapeutic applications, Biotechnol Genet Eng Rev 2008 25:93-112.
Kalahnikova et al., Development of a strategy of influenza virus separation based on pseudoaffinity chromatography on short monolithic columns, Analytical Chemistry 2008 80(6):2188-2198.
Li et al., Carboydrate-fuctionalized chitosan fiber for influenza virus capture, Biomacromolecules 2011 12(11):3962-3969.

(Continued)

*Primary Examiner* — Stacy B Chen
(74) *Attorney, Agent, or Firm* — Reza Mollaaghababa; Thomas J. Engellenner; Pepper Hamilton LLP

(57) ABSTRACT

Material complexes that capture biologicals and methods of synthesizing and using such complexes composed of fluid-insoluble material and a receptor are provided herewith. The fluid-insoluble material has reactive functionality on its surface, including hydroxyl, amino, mercapto or epoxy functionality material. The material can be agarose, sand, textile, or any combination thereof. The receptor is selected from the group consisting of mono- and poly-saccharides, heparin, or any combination thereof. Also provided are methods whereby releasing the captured biologicals is controllable.

11 Claims, 9 Drawing Sheets

(56) References Cited

OTHER PUBLICATIONS

Figure 1:
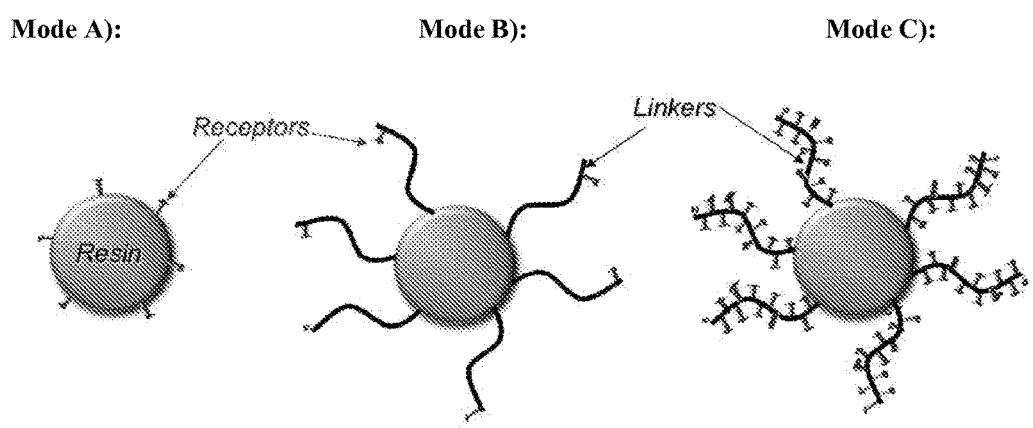

Chinese Second Office Action w/English Translation received in corresponding Chinese Application No. 201480014377.0 dated Oct. 30, 2017; 11 pages.
International Search Report and Written Opinion received in PCT/US2014/26540 dated Jul. 28, 2014; 11 pages.
International Preliminary Report on Patentability received in PCT/US2016/28399 dated Nov. 2, 2017; 6 pages.
International Search Report and Written Opinion received in PCT/US2016/28399 dated Jul. 26, 2016; 7 pages.
Office Action received in U.S. Appl. No. 14/773,059 dated Apr. 17, 2017; 18 pages.
Simons et al., "Monodispere perfluorohexane emulsions for targeted ultrasound contrast imaging" Journal of Materials Chemistry, vol. 20, pp. 3918-3923, (Mar. 12, 2010).
Medintz et al. "Proteolytic Activity Monitored by Fluorescence Resonance Energy Transfer Through Quantum-dot-peptide Conjugates", Nature Materials, vol. 5, pp. 581-589 (2006).
Chinese Office Action with English Translation for related Chinese Patent Application No. 201480014377.0, dated Jul. 23, 2018, 13 pages.

\* cited by examiner

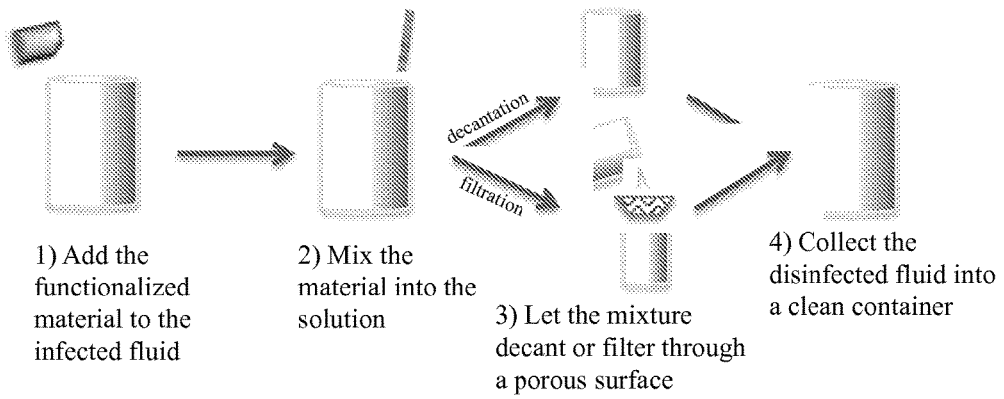

1) Add the functionalized material to the infected fluid
2) Mix the material into the solution
3) Let the mixture decant or filter through a porous surface
4) Collect the disinfected fluid into a clean container

Figure 2A

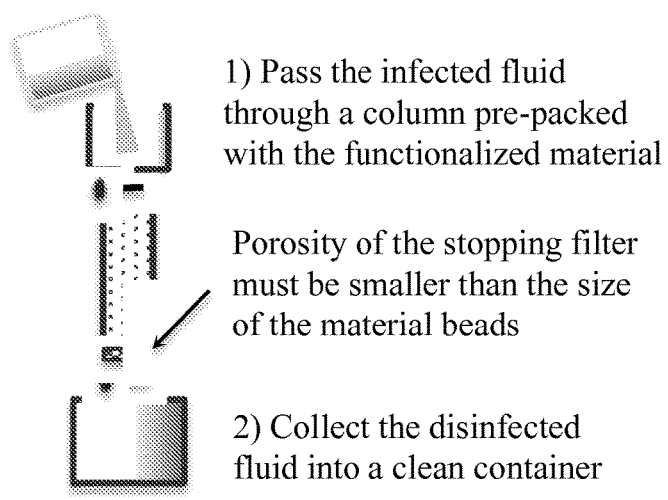

1) Pass the infected fluid through a column pre-packed with the functionalized material Porosity of the stopping filter must be smaller than the size of the material beads 2) Collect the disinfected fluid into a clean container

Figure 2B

Lactose attachment to Sand:

Lactose attachment to Sepharose:

Lactose attachment to Poly(glycidyl methacrylate):

Lactose attachment to sand through a branched linker:

Lactose attachment to Sepharose through a branched linker:

Lactose attachment to Poly(glycidyl methacrylate) through branched linkers:
C-1) through a hyperbranched dendrimer:
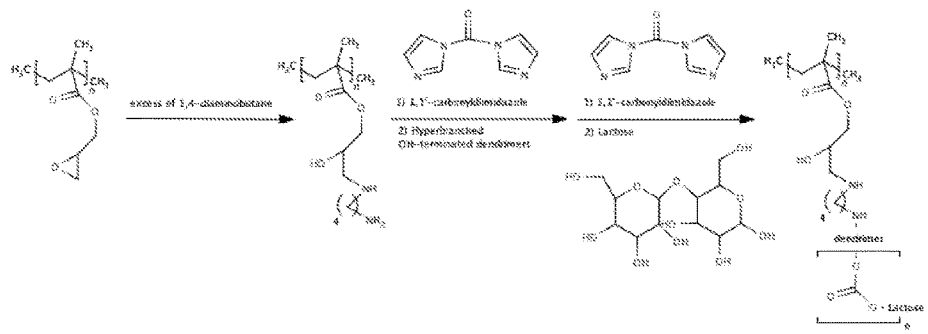
C-2) and through chitosan:
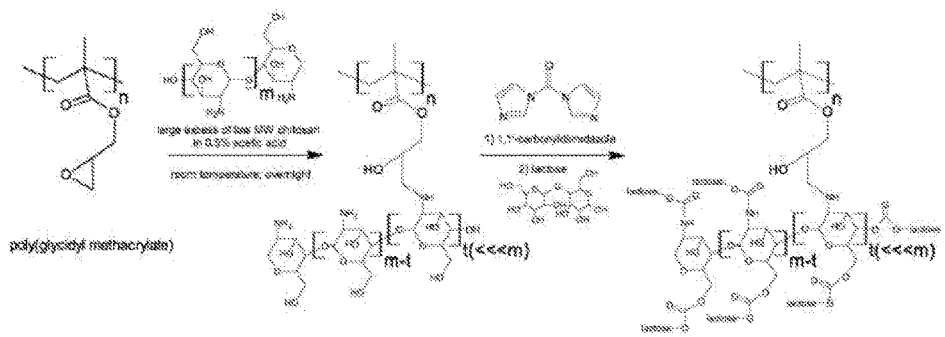
Figure 5C

*When X=O and Y=O, the product is a carbonate derivative.*
*When X=NH and Y=O, the product is a carbamate derivative.*
*When X=NH and Y=NH, the product is a urea derivative.*

*HA=hemagglutinin, PGMA=poly(glycidyl methacrylate), Ch=chitosan*

*PGMA=poly(glycidyl methacrylate), Ch=chitosan, SL=sialyllactose, L=lactose*

METHODS AND MATERIALS FOR MICROORGANISM CAPTURE

CROSS-REFERENCE TO RELATED APPLICATIONS

This application is a 35 U.S.C. § 371 national phase application of PCT Application No. PCT/US2014/026540, filed Mar. 13, 2014, which claims priority to U.S. Provisional Application No. 61/784,432, filed Mar. 14, 2013, each of which is incorporated herein by reference in its entirety.

FIELD

The present disclosure is directed to fluid-insoluble material complexes that control the biological composition of fluids, and methods of manufacturing and using the same.

BACKGROUND

Affinity ligand-matrix conjugates for use as chromatography adsorbents for protein purification are well established. For example, the use of phenyl-based ligand for protein purification, including purification of the in-demand monoclonal antibodies has been disclosed in the patent literature. Other known affinity ligands used in chromatography media to purify influenza A are fusion peptides and lectin. Also, studies on distancing ligands from matrix cores have been described.

Alternative methods for purifying influenza A include, for example, size exclusion and ion exchange chromatographies.

SUMMARY

The present disclosure provides methods of manufacturing and using fluid-insoluble material complexes that specifically capture microorganisms, proteins, and other biologicals and remove them from fluids. It also pertains to the option of controllably releasing the captured biologicals under certain conditions.

Some embodiments pertain to methods of immobilizing a biological by mixing a sample containing the biological with a material complex and physically separating the immobilized biological from the sample. The biological is immobilized by its adsoption to the material complex. The physical separation of the immobilized biological from the rest of the sample can be achieved by such methods as decantation, for example relying on gravity or magentic forces, and filtration. The material complex can include a hydroxyl-, amino-, mercapto- or epoxy-containing material that is fluid-insoluble and at least one receptor bound to the material. The biological can include, for example, any of a cell, tissue, tissue product, blood, blood product, protein, vaccine, antigen, antitoxin, virus, microorganism, fungus, yeast, alga, and/or bacterium. The immobilized biological can then be extracted from the material complex, such as by elution. In the case of the virus, the extracted biological can then be included in a vaccine treatment. In the case of the protein, the extracted biological can then be included in a vaccine or therapeutic treatment.

Some embodiments pertain to material complexes composed of fluid-insoluble material and a receptor. The material can be agarose, sand, textile, or any combination thereof. The fluid-insoluble material has reactive functionality on its surface, including hydroxyl, amino, mercapto or epoxy functionality material. The receptor is selected from the group consisting of mono- and poly-saccharides, heparin, or any combination thereof. In some embodiments, the composition can include a linker bridging between the material and the receptor. The linker is covalently bonded to the material and the receptor. The linker can be a linear or branched small molecule or polymer.

Some embodiments pertain to methods of manufacturing a composition comprising attaching a receptor on a hydroxyl-containing material, an epoxy-containing material, and an amino-containing material. The receptor can be lactose. The material can be sand, agarose, poly(glycidyl methacrylate) (PGMA), or PGMA-$NH_2$.

BRIEF DESCRIPTION OF THE DRAWINGS

The appended drawings have been included herein so that the features recited herein, advantages and objects of the disclosure will become clear and can be understood in detail. These drawings form a part of the specification. It is to be noted, however, that the appended drawings illustrate suitable embodiments and should not be considered to limit the scope of the disclosure.

FIG. 1 illustrates three different embodiments; fluid-insoluble material cores are complexed with receptors either directly or indirectly through linkers.

FIGS. 2A and 2B illustrate material complexes for fluid disinfection.

FIG. 3 illustrates the use of material complexes in affinity chromatography to concentrate micro-organisms in solutions.

FIGS. 4A, 4B, and 4C illustrate examples of direct attachment of receptors to materials.

FIGS. 5A, 5B, and 5C illustrate examples of attachment of receptors to materials via linkers.

FIG. 6 illustrates a general route for covalent coupling when using 1,1'-carbonyldiimidazole.

FIG. 7 illustrates quantification of the binding of recombinant hemagglutinin to insoluble materials in PBS buffer; quantification was performed using the Bradford Protein Assay by measuring absorbance at 595 nm wavelength.

FIG. 8 illustrates quantification of influenza A attachment to insoluble materials.

FIG. 9 illustrates the activity of a complex of PGMA polymer while varying the initial titer of influenza A.

DESCRIPTION

The present disclosure is directed to synthesizing and using fluid-insoluble material complexes that specifically capture biologicals and remove them from fluids. It also pertains to the option of controllably releasing the captured biologicals under specific conditions.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this disclosure adhere to standard definitions generally accepted by those having ordinary skill in the art. In case any further explanation might be needed, some terms have been further elucidated below.

The term "biologicals" as used herein refers to living organisms and their products, including, but not limited to, cells, tissues, tissue products, blood, blood products, proteins, vaccines, antigens, antitoxins, viruses, microorganisms, fungi, yeasts, algae, bacteria, etc., or any combination thereof. One example of a biological can include microorganisms, such as pathogenic or non-pathogenic bacteria. Another example of biologicals can include viruses, viral products, virus-imitating entities, or any combination thereof. In some embodiments, the biological is selected from the group consisting of cell, tissue, tissue product, blood, blood product, body fluid, product of body fluid, protein, vaccine, antigen, antitoxin, biological medicine, biological treatment, virus, microorganism, fungus, yeast, alga, bacterium, prokaryote, eukaryote, *Staphylococcus aureus*, *Streptococcus*, *Escherichia coli* (*E. coli*), *Pseudomonas aeruginosa*, mycobacterium, adenovirus, rhinovirus, smallpox virus, influenza virus, herpes virus, human immunodeficiency virus (HIV), rabies, chikungunya, severe acute respiratory syndrome (SARS), polio, malaria, dengue fever, tuberculosis, meningitis, typhoid fever, yellow fever, ebola, shingella, listeria, Yersinia, West Nile virus, protozoa, fungi *Salmonella enterica*, *Candida albicans*, *Trichophyton mentagrophytes*, poliovirus, *Enterobacter aerogenes, Salmonella typhi, Klebsiella pneumonia, Aspergillus brasiliensis*, and methicillin resistant *Staphylococcus aureus* (MRSA), or any combination thereof.

In some embodiments, fluid-insoluble materials can be complexed with microoganism-capturing groups ("receptors"), the structures of which are drawn from natural cellular receptors, antibodies, or simply from available data describing microorganism interaction with soluble molecules. The receptors can be directly attached to the material (FIG. 1, Mode A) or through a linker (FIG. 1, Mode B). In order to protect the integrity of the molecular structure of the subject material complexes, particularly when re-cycling is a requirement, one method of inter-connecting the receptors, linkers and materials can be via covalent bonding. For certain applications where added structural stability is not needed, for example in case of single use material complexes, physical bonding can substitute covalent bonding. The receptors play a direct role by capturing the microorganims through physical bonding. One role of the linkers is to position the receptors at an active distance from the core of the material. By distancing the receptors from the core of the material, the receptors can easily access the target microorganisms. Another role for the linkers, particularly when they are branched, is to increase the density of the receptors on the surface of the material (FIG. 1, Mode C). Increase in the density of receptors correlates with an increase in the capacity of capturing higher concentrations of microorganisms.

Representative examples of the three main components of the material complexes are: 1) materials: agarose, sand, textiles (such as cellulose/cotton, wool, nylon, polyester), metallic particles (including nanoparticles), magnetic particles (including nanoparticles), glass, fibergalss, silica, wood, fiber, plastic, rubber, ceramic, percelain, stone, marble, cement, biological polymers, natural polymers and synthetic polymers (such as PGMA), or any combination thereof; 2) receptors: lactose (natural and synthetic) and its derivatives (such as sialyllactose), mono- and poly-saccharides (natural and synthetic), heparin and chitosan, or any combination thereof; and 3) linkers: linear and branched polymers, such as poly(ethylene glycol) (PEG) and poly (ethylenimine) (PEI, various ratios of primary:secondary: tertiary amine groups), (e.g. multi-arm branched PEG-amines), dendrons and dendrimers (e.g. liyperbranched bis-MPA polyester-16-hydroxyl) and chitosan, or any combination thereof. Each of the material complexes may incorporate the material and the receptor components. However, incorporating the linker component is optional.

Suitable metal materials include, but are not limited to, stainless steel, nickel, titanium, tantalum, aluminum, copper, gold, silver, platinum, zinc, Nitinol, Inconel, iridium, iron, tungsten, silicon, magnesium, tin, alloys, coatings containing any of the foregoing, galvanized steel, hot dipped galvanized steel, electrogalvanized steel, annealed hot dipped galvanized steel, or any combination thereof.

Suitable glass materials include, but are not limited to, soda lime glass, strontium glass, borosilicate glass, barium glass, glass-ceramics containing lanthanum, or any combination thereof.

Suitable sand materials include, but are not limited to, sand comprised of silica (e.g., quartz, fused quartz, crystalline silica, fumed silica, silica gel, and silica aerogel), calcium carbonate (e.g., aragonite), or any mixture thereof. The sand can comprise other components, such as minerals (e.g., magnetite, chlorite, glauconite, gypsum, olivine, garnet), metal (e.g., iron), shells, coral, limestone, and rock, or any combination thereof.

Suitable wood materials include, but are not limited to, hard wood and soft wood, and materials engineered from wood, wood chips, or fiber (e.g., plywood, oriented strand board, laminated veneer lumber, composites, strand lumber, chipboard, hardboard, medium density fiberboard). Types of wood include alder, birch, elm, maple, willow, walnut, cherry, oak, hickory, poplar, pine, fir, or any combination thereof.

Suitable fiber materials include, but are not limited to, natural fibers (e.g., derived from an animal, vegetable, or mineral) and synthetic fibers (e.g., derived from cellulose, mineral, or polymer). Suitable natural fibers include cotton, hemp, jute, flax, ramie, sisal, bagasse, wood fiber, silkworm silk, spider silk, sinew, catgut, wool, sea silk, wool, mohair, angora, and asbestos, or any combination thereof. Suitable synthetic fibers include rayon, modal, and Lyocell, metal fiber (e.g., copper, gold, silver, nickel, aluminum, iron), carbon fiber, silicon carbide fiber, bamboo fiber, seacell, nylon, polyester, polyvinyl chloride fiber (e.g., vinyon), polyolefin fiber (e.g., polyethylene, polypropylene), acrylic polyester fiber, aramid, spandex, or any combination thereof.

Suitable natural polymer materials include, but are not limited to, a polysaccharide (e.g., cotton, cellulose), shellac, amber, wool, silk, natural rubber, and a biopolymer (e.g., a protein, an extracellular matrix component, collagen), or any combination thereof.

Suitable synthetic polymer materials include, but are not limited to, polyvinylpyrrolidone, acrylics, acrylonitrile-butadiene-styrene, polyacrylonitrile, acetals, polyphenylene oxides, polyimides, polystyrene, polypropylene, polyethylene, polytetrafluoroethylene, polyvinylidene fluoride, polyvinyl chloride, polyethylenimine, polyesters, polyethers, polyamide, polyorthoester, polyanhydride, polysulfone, polyether sulfone, polycaprolactone, polyhydroxy-butyrate valerate, polylactones, polyurethanes, polycarbonates, polyethylene terephthalate, as well as copolymers thereof, or any combination thereof.

Suitable rubber materials include, but are not limited to, silicones, fluorosilicones, nitrile rubbers, silicone rubbers, polyisoprenes, sulfur-cured rubbers, butadiene-acrylonitrile rubbers, isoprene-acrylonitrile rubbers, and the like, or any combination thereof.

Suitable ceramic materials include, but are not limited to, boron nitrides, silicon nitrides, aluminas, silicas, and the like, or any combination thereof.

Suitable stone materials include, but are not limited to, granite, quartz, quartzite, limestone, dolostone, sandstone, marble, soapstone, serpentine, or any combination thereof.

Exemplary receptors can include: 1) heparin, a negatively charged polymer that can mimic innate glycosaminoglycanes found in the memebranes of host cells. It is commercially available as heparin sodium which is extracted from porcine intestinal mucosa and is approved as blood anticoagulant. Also, non-animal-derived synthetic heparin-mimicking sulfonic acid polymers can act in a similar fashion to natural heparin; 2) chitosan, an ecologically friendly bio-pesticide that can ligate to a variety of microorganisms and proteins. It is also used as a hemostatic agent and in transdermal drug delivery; and 3) lactose, a by-product of the dairy industry. It is widely available and produced annually in millions of tons. Lactose can also be synthesized by condensation/dehydration of the two sugars, galactose and glucose, including all their isomers.

Exemplary materials can include: 1) sand, an affordable and widely available material. In addition, complexed sand could easily replace non-complexed sand in established technologies such as drinking water purification; 2) agarose, particularly Sepharose®, a beaded polysaccharide polymer extracted from seaweed. They are also widely available and used in chromatography to separate biomolecules; and 3) PGMA, a synthetic polymer produced from Glycidyl methacrylate, which is an ester of methacrylic acid and a common monomer used in the production of epoxy materials.

Exemplary linkers can include: 1) chitosan, see its description as a receptor; 2) Poly(ethylene glycol) and its derivatives, produced from ethylene oxides with many different chemical, biological, commercial and industrial uses; and 3) dendrons and dendrimers, relatively new molecules. They are repetitively branched molecules using a small number of starting reagents. They are commonly used in drug delivery and in sensors.

In some embodiments, the receptors can be directly attached to the material (FIG. 4) or through linkers (FIG. 5) via chemical coupling. One type of coupling reagent is 1,1'-carbonyldiimidazole (CDI). The coupling reagent may also be N,N'-Dicyclohexylcarbodiimide (DCC) or N-(3-Dimethylaminopropyl)-N'-ethylcarbodibide hydrochloride (EDC or EDCI).

Figure 6:
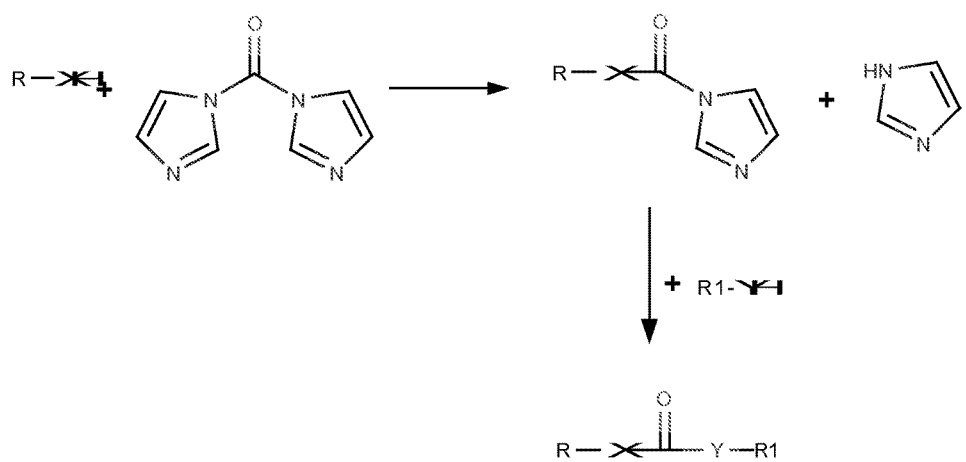

An exemplary coupling reagent is CDI. Basic protonated end groups, such as hydroxyl groups (R—OH) in sand and Sepharose® and tertiary amine groups (R—NH$_2$) in PGMA-diaminobutane, readily react with CDI to form an ester or amide link. The resulting imidazole-substituted derivatives are reacted with hydroxyl-terminated receptors yielding either carbonates [R—O—C(O)—O-receptor] or carbamates [R—N(H)—C(O)—O-receptor]. The resulting imidazole-substituted derivatives can also be reacted with amine-terminated receptors yielding urea derivatives [R—N(H)—C(O)—N(H)-receptor] (FIG. 6). Due to the formation of a covalent bond between the receptor and the material (direct bonding or through a linker), the structure of the bound receptor is different compared to the structure of the commercially available free receptor. For example, as depicted in FIG. 6, the receptor looses a hydrogen atom upon reaction with the immidazole-substituted derivatives to form a receptor-carbonate, receptor-carbamate or receptor-urea derivative.

If an appropriate functional group is not present on the surface of the material, a suitable functional group can be made available of the surface by a chemical transformation. In general, a chemical transformation can be hydrolysis, oxidation (e.g., using Collins reagent, Dess-Martin periodinane, Jones reagent, and potassium permanganate), reduction (e.g., using sodium borohydride or lithium aluminum hydride), alkylation, deprotonation, electrophilic addition (e.g., halogenation, hydrohalogenation, hydration), hydrogenation, esterification, elimination reaction (e.g., dehydration), nucleophilic substitution, radical substitution, or a rearrangement reaction. If needed, more than one chemical transformation, successively or simultaneously, can be used to provide a suitable functional group or a heterogeneous group of functional groups of various identities. Alternatively, a monomer with a desired functional group can be grafted to the material.

In some embodiments, the chemical transformation is hydrolysis. Generally, the hydrolysis is performed with water in the presence of a strong inorganic, organic, or organo-metallic acid (e.g., strong inorganic acid, such as hydrochloric acid, sulfuric acid, phosphoric acid, nitric acid, hydroiodic acid, hydrobromic acid, chloric acid, and perchloric acid) or strong inorganic, organic, or organo-metallic base (e.g., Group I and Group II hydroxides, such as lithium hydroxide, sodium hydroxide, potassium hydroxide, rubidium hydroxide, cesium hydroxide, magnesium hydroxide, calcium hydroxide, and barium hydroxide; ammonium hydroxide; and sodium carbonate). For example, a material comprising an acyl halide can undergo hydrolysis to form a carboxylic acid.

In some embodiments, the chemical transformation is a substitution reaction where one functional group is replaced with another. For example, a material comprising a haloalkyl group can react with a strong base to form a hydroxy group.

In some embodiments, the chemical transformation is alkylation, hydrogenation, or reduction. For example, a material comprising a hydroxy or haloalkyl (e.g., iodoalkyl or bromoalkyl) moiety can be reacted with ammonia to form an amino group. A material comprising a haloalkyl moiety also can be converted to a mercapto group by S-alkylation using thiourea. A material comprising a nitrile can be hydrogenated to form an amino group. A material comprising an amido group can be reduced (e.g., in the presence of lithium aluminum hydride) to form an amino group. A material comprising a formyl or keto group can be reduced to form an amino or hydroxy group. Multiple homogeneous or heterogeneous transformations can be applied simultaneously or successively.

The material complexes can be formed by any suitable method using suitable temperatures (e.g., room temperature, reflux), reaction times, solvents, catalysts, and concentrations. In some embodiments, an excess amount of linkers and receptors will be used to ensure an effective amount of receptors in the material complexes.

In some embodiments, attachments amongst receptors, linkers, and materials can be secured physically. This is achieved by mixing receptors or linkers, or combinations thereof, dissolved in solvents with the materials, then allowing the solvents to evaporate in air or under vacuum.

The receptors may also reversibly interact with the target biologicals, such as micro-organisms or virus. The biologicals can be desorbed from the receptors, such as through elution. Eluents such as higher-then-physiological sodium chloride solutions and lactose-containing solutions are capable of desorbing the biological from the material complexes.

Depicted in FIGS. 4 and 5, one common receptor is lactose Immobilized lactose can be used for capturing a high titer of influenza A virus. Furthermore, lactose-PGMA combination is also an exemplary material.

The material complexes can be used for the removal of biologicals from fluids and in affinity chromatography set-ups. These material complexes should not dissolve in the aforementioned fluids and are expected to reduce or eliminate the generation of harmful chemical or biological byproducts. The material complexes can be used in a batch setup (FIG. 2A) or in a flow setup (FIG. 2B). In a batch setup, the material complexes are added to the fluids and then separated by decantation or filtration. In a flow setup, the fluids are circulated through one or multiple cartridges containing the material complexes. In the flow setup, the cartridges are stopped with filters, the porosity of which is smaller than the size of the material complexes. Such small porosity stops the material complexes from escaping the cartridges.

Figure 3:
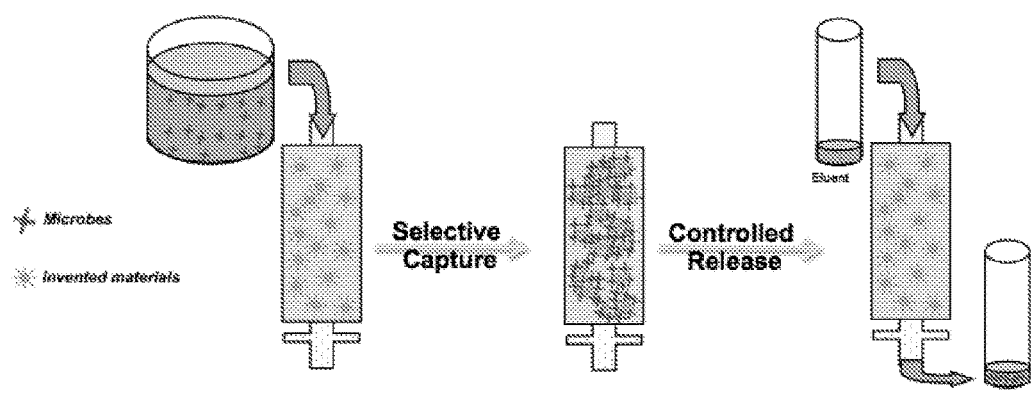

Affinity chromatography may also involve the separation and potentially purification of target biologicals from a complex mixture based on a reversible adsorption of the desired biologicals onto the chromatographic matrix. Where the disclosed material complexes are used to purify biologicals, such as microbes and proteins for vaccine and therapeutic drug manufacturing, the biological-containing solutions may be passed through the material complexes packed in a cartridge (FIG. 3). While the target biologicals are expected to bind to the material complexes, the impurities are expected to pass through the cartridge without binding to the material complexes. The next step is the elution of the bound target biologicals off of the material complexes using impurity-free eluents. Depending on the titer of the biological and its affinity to material complexes, the process of biological separation, purification, or combinations thereof, can be achieved by multiple circulations through the same cartridge or passage through successive cartridges.

The disclosed methods and material complexes may be used in a number of applications including, for examples: 1) pharmaceuticals: purification of vaccines, proteins, including monoclonal antibodies (MAbs), and other biologicals; 2) diagnostics: increasing the concentration of target biologicals in samples leading to increase in sensitivity in existing and novel diagnostic tools, or including materials that change color upon binding a biological molecule allowing simple point-of-use diagnostics; 3) prophylactics: trapping biologicals prior to infection or contamination (e.g. face masks, air purifiers, gloves); 4) therapeutics: disinfection of blood and its products, extracorporeal dialysis, disinfection of intestinal fluids, and controlling the biological composition of life-sustaining fluids; and 5) environmental: removing biologicals from water and other fluids in the environment, including air.

In some embodiments, the disclosed methods and material complexes can be used for vaccine purification. Current vaccine purification techniques use a combination of membrane separation, such as ultrafiltration, and chromatographic separation, such as size exclusion and ion exchange. While the overall purity is above about 90%, the yield is only about 50%. The disclosed methods and material complexes can substitute the separations based on size exclusion, ion exchange chromatography, or combinations thereof. If the disclosed methods and material complexes show high selectivity towards the target biologicals, then it is possible that the disclosed methods and material complexes could substitute both chromatograpic separations as well as the membrane separation and other filtration steps, and combinations thereof.

In some embodiments, the disclosed methods and material complexes can be used for water disinfection. Current water disinfection techniques are based on irradiation with UV light, use of ozone, or use of bleaching chemicals designed to kill viruses and bacteria. Unfortunately, the UV light technique and generation of ozone are both very energy consuming, and the chemicals that kill viruses and bacteria are also harmful to humans. Moreover, many of the chemical and biological by-products that result from these disinfection techniques can cause serious diseases, such as cancer and damage to the nervous system. The disclosed methods and material complexes can disinfect water at a relatively low cost and without inducing such side effects. Two application methods can be followed to disinfect water, batch and flow setups (FIG. 2). In the case of water disinfection application, some exemplary receptors may be heparin and chitosan.

In some embodiments, the disclosed methods and material complexes can be used for pathogen inactivation in transfusion blood. Reduction of infectious entities and controlling the biological composition in transfusion blood without compromising the blood quality is the target of various techniques, particularly the proactive pathogen inactivation techniques. Current methods include Solvent Detergent (SD), heat treatments and use of photosensitive chemicals. However, these techniques induce changes in normal blood composition leading to post-transfusion side effects. For example, plasma pasteurization denatures clotting factors, SD treatment results in loss of $\alpha_2$-antiplasmin crucial in hemostasis, and photosensitive chemicals are immunogenic, lower platelet count increment in recipients, and generate chemical by-products. Moreover, following deactivation of, for example, HIV-1, the basic peptides released, HIV-1's Tat (transactivating factor) and gp120, induce AIDS-associated pathologies. The disclosed methods and material complexes may result in pathogen inactivation while avoiding such side effects. One method may include mixing or passing a sample, such as viremic allogeneic blood or its products, or combinations thereof, with or through the material complexes. The material complexes can be packed in a cartridge, i.e. flow setup, or be mixed with the sample, i.e. batch setup. Then, the mixture of sample and material complex can be filtered through a membrane filter. Depending on the viral titer and the viral affinity: 1) the flow setup can include multiple circulations through the same packed cartridge or passage through successive cartridges; and 2) the batch setup can include successive mixing of the sample with multiple beds of fresh material complexes. In the case of pathogen inactivation in transfusion blood, one receptor may be heparin.

In some embodiments, the disclosed methods and material complexes can be used for purification of viruses, such as an influenza vaccine, or virus-imitating particles. The materials currently used to purify influenza vaccines are either poorly selective and cheap to produce or highly selective and expensive to produce. The former class of materials for vaccine purification is dominated by non-selective chemistry-based materials, while the later class of materials for vaccine purification is dominated by highly selective biology-based materials. The former non-selective materials lead to low yield and low purity, two major setbacks in vaccine manufacturing. The main shortcomings of the latter group of materials, which include immobilized antibodies, are: 1) expense; 2) the requirement for re-qualification after each recycling; and 3) degradation of the immobilized biological molecules over time. The disclosed material complexes are inexpensive chemistry-based materials that are capable of matching the selectivity to biology-based materials. In the case of influenza vaccine purification applications, some receptors include lactose (natural and synthetic) and its derivatives.

The present disclosure is also directed to kits comprising any one or more of the material complexes disclosed herein, and/or reagents used for making and/or using them.

The present disclosure is also directed to products comprising any of the compositions disclosed herein. In some embodiments, the product is selected from a vaccine, medical device, diagnostic equipment, implant, glove, mask, textile, surgical drape, tubing, surgical instrument, safety gear, fabric, apparel item, floor, handle, wall, sink, shower, tub, toilet, furniture, wall switch, toy, athletic equipment, playground equipment, shopping cart, countertop, appliance, railing, door, air filter, air processing equipment, water filter, water processing equipment, pipe, phone, cell phone, remote control, computer, mouse, keyboard, touch screen, leather, cosmetic, cosmetic making equipment, cosmetic storage equipment, personal care item, personal care item making equipment, personal care storage equipment, animal care item, animal care item making equipment, animal care storage equipment, veterinary equipment, powder, cream, gel, salve, eye care item, eye care item making equipment, eye care storage equipment, contact lens, contact lens case, glasses, jewelry, jewelry making equipment, jewelry storage equipment, utensil, dish, cup, container, object display container, food display container, food package, food processing equipment, food handling equipment, food transportation equipment, food storage equipment, food vending equipment, animal housing, farming equipment, animal food handling equipment, animal food storage space, animal food processing equipment, animal food storage equipment, animal food container, air vehicle, land vehicle, water vehicle, water storage space, water storage equipment, water storage container, water processing equipment, water storage equipment, water filter, and air filter, or any combination thereof.

The methods and material complexes described herein are designed to capture complete biologicals, such as viruses, microorganisms and bacteria, and physically remove them from the original sample. The captured biologicals can be released from the material complexes by elution using a release solutions or eluents capable of desorbing the captured biologicals from the material complexes, such as higher-then-physiological sodium chloride solutions or lactose solutions.

U.S. Provisional Application Ser. No. 61/784,432 filed Mar. 14, 2013 is incorporated herein by reference in its entirety.

EXAMPLES

Example 1

Figure 4A:
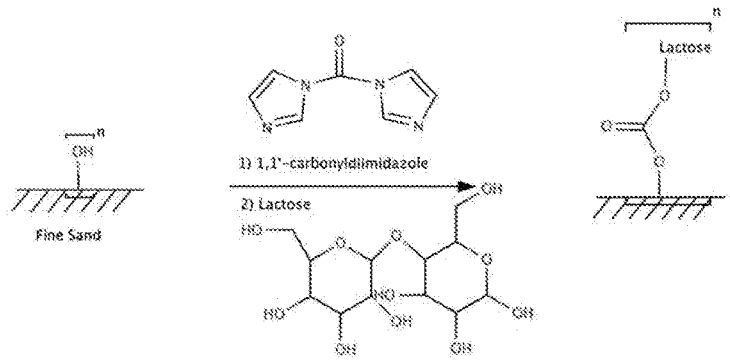

Synthesis of Lactose-Sand (FIG. 4A)

The synthesis followed these steps: 5 grams of fine sand was rinsed with 20 ml DI water while on a medium frit filter. They were then mixed with 10 ml pH 8.5 (20 mM) borate buffer and allowed to stir for 10 minutes at room temperature. Thirty nine mg of 1,1'-carbonyldiimidazole (0.24 mmol, MW 162.15) was then added to the suspension and allowed to react for 2 hours before adding 190 mg of β-D-lactose (0.55 mmol). The resulting mixture was allowed to stir for 4 days at room temperature. The final suspension was filtered and the solid was rinsed with de-ionized (DI) water. The wetness of the solid was preserved.

Example 2

Figure 4B:
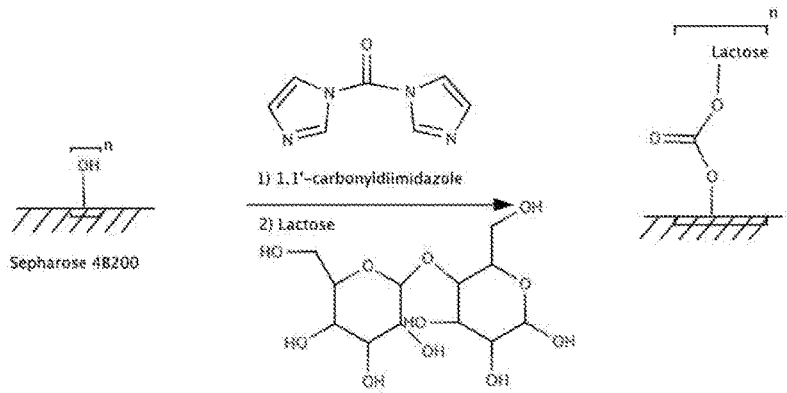

Synthesis of Lactose-Sepharose® (FIG. 4B)

The synthesis followed these steps: 5 grams of wet Sepharose (ca. 5 wt % in water) was mixed with 10 ml pH 8.5 (20 mM) borate buffer and allowed to stir for 10 minutes at room temperature. Thirty nine mg of 1,1'-carbonyldiimidazole (0.24 mmol, MW 162.15) was then added to the suspension and allowed to react for 2 hours before adding 190 mg of β-D-lactose (0.55 mmol). The resulting mixture was allowed to stir for 4 days at room temperature. The final suspension was filtered and the solid was rinsed with 100 ml DI water. The wetness of the solid was preserved.

Example 3

Figure 4C:
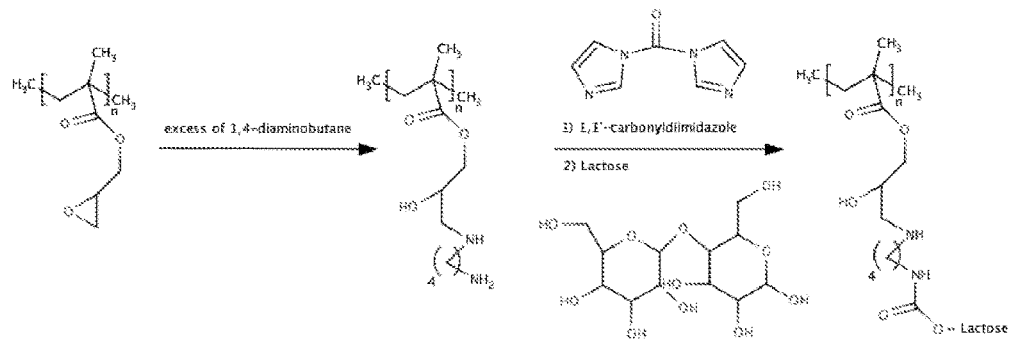

Synthesis of Lactose-PGMA (FIG. 4C)

The synthesis followed these steps: A 100 ml single neck round bottom flask and a magnetic bar were dried under vacuum while hot. Fifty ml dry tetrahydrofuran was added followed by 1.24 g (14 mmol) of 1,4-diaminobutane. While stirring the solution, 200 mg PGMA (1.4 mmol equivalents of the repeat unit) was added. The solution was then allowed to stir at room temperature for 10 minutes before starting the in-situ evacuation into a cold trap, using the vacuum line. The reaction flask was gently heated using a heating gun in order to ensure the removal of all volatile reagents. To the resulting oil-like product, 50 ml DI water were added leading to the precipitation of a white film-like solid. This solid was then filtered on a medium frit and rinsed with 300 ml DI water. The yield was 0.529 g of PGMA-NH$_2$. The final polymer was efficiently dried and stored at low temperature.

One hundred and ten mg of the resulting intermediate, PGMA-NH$_2$, was mixed with 10 ml pH 8.5 20 mM borate buffer and allowed to stir for few minutes at room temperature. Nineteen mg of 1,1'-carbonyldiimidazole was then added to the suspension and allowed to stir for 1 hour before adding 0.055 g of β-D-lactose. The final mixture was allowed to stir for two days at room temperature followed by filtering through a medium frit and rinsing with 50 ml DI water. The wetness of the solid was preserved.

Example 4

Figure 5A:
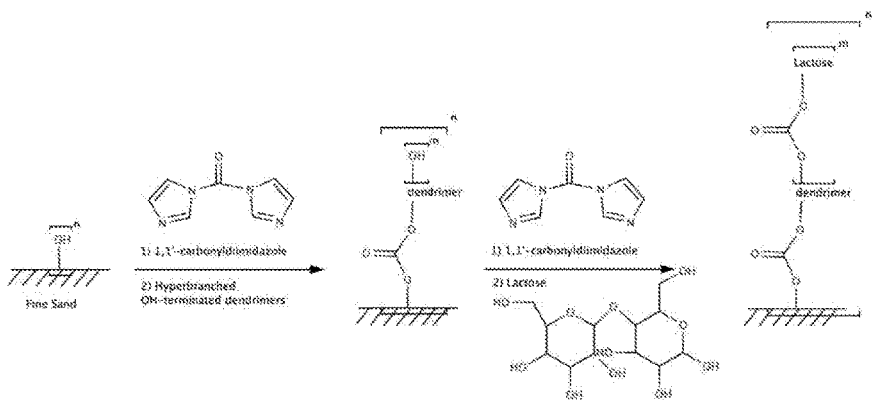

Synthesis of Lactose-[branching]-Sand (FIG. 5A)

The synthesis followed these steps: Five grams of fine sand was vigorously stirred with 20 ml DI water, then filtered through a medium frit. They were then mixed with 10 ml pH 8.5 20 mM borate buffer and allowed to stir for few minutes at room temperature. Sixteen mg of 1,1'-carbonyldiimidazole (0.1 mmol, MW 162.15) was then added to the suspension and allowed to stir for 2 more hours before adding 0.25 g of Hyperbranched bis-MPA polyester-16- hydroxyl (0.1425 mmol, 228 mmol. eq. OH). After two additional hours, 0.37 g (2.28 mmol) of 1,1'-carbonyldiimidazole was added to the suspension and allowed to stir for 2 more hours before adding 3.9 g (11.4 mmol) of β-D-lactose. Five ml of the pH 8.5 borate buffer was then added. The final "almost clear" mixture was allowed to stir for two days at room temperature. The final solution was filtered through a medium frit and rinsed with 50 ml DI water, isolating 4.8943 g of sand complex the color of which was similar to that of the starting sand. The wetness of the solid was preserved.

Example 5

Figure 5B:
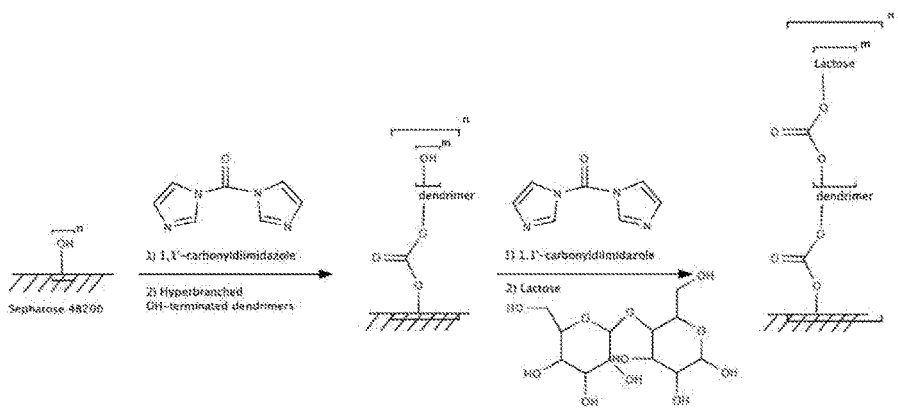

Synthesis of Lactose-[branching]-Sepharose (FIG. 5B)

The synthesis followed these steps: One gram of wet Sepharose (ca. 5 wt % in water) was mixed with 10 ml pH 8.5 20 mM borate buffer and allowed to stir for few minutes at room temperature. Thirty two mg of 1,1'-carbonyldiimidazole (0.2 mmol, MW 162.15) was then added to the suspension and allowed to stir for 2 more hours before adding 0.5 g of Hyperbranelted bis-MPA polyester-16-hydroxyl (0.285 mmol, 4.56 mmol.eq. OH). After two additional hours, 0.74 g (4.56 mmol) of 1,1'-carbonyldiimidazole was added to the suspension and allowed to stir for 2 hours before adding 7.8 g (22.8 mmol) of β-D-lactose. Additional 5 ml of the pH 8.5 buffer was added. The final white mixture was allowed to stir for two days at room temperature. Fifty ml DI water were added to the final dense white solution to ensure dissolution of all free reagents. The final solution was filtered through a medium frit and rinsed with 50 ml DI water. The wetness of the solid was preserved.

Example 6

Synthesis of Lactose-[branching]-PGMA (FIG. 5C, 1)

The synthesis, including a dendrimer, followed these steps: One hundred mg of PGMA-NH$_2$ (0.4 mmol equivalents of the repeat unit) was mixed with 50 ml pH 8.5 20 mM borate buffer and allowed to stir for few minutes at room temperature. Sixty four mg of 1,1'-carbonyldiimidazole (0.4 mmol, MW 162.15) was then added to the suspension and allowed to stir for 2 hours before adding 1 g of Hyperbranched bis-MPA polyester-16-hydroxyl (0.57 mmol, 9.12 mmol.eq. OH). After two additional hours, 1.48 g (9.12 mmol) of 1,1'-carbonyldiimidazole was added to the suspension and allowed to stir for 2 more hours before adding 15.6 g (45.6 mmol) of β-D-lactose. The final white mixture was allowed to stir for two days at room temperature. Fifty ml DI water was added to the final dense white solution to ensure dissolution of all free reagents. The final solution was filtered through a medium frit and rinsed with 50 ml DI water. The wetness of the solid was preserved.

Example 7

Synthesis of Lactose-[branching]-PGMA (FIG. 5C, 2)

The synthesis, including chitosan, followed these steps: Four hundred ml of 0.5% acetic acid in DI water was prepared by adding 2 g of the acid to 400 mL of water. To this acid solution, 2 g of Chitosan was added and the solution was allowed to stir at room temperature for 5 minutes until becoming monophasic. Then, 200 mg of PGMA was added and the final suspension was allowed to stir at room temperature for two hours. The final off-white suspension was then filtered through a medium frit and the solid was washed with 100 ml of DI water. The isolated solid was re-suspended in 10 ml DI water. Its pH was ca. 4. One drop of a sodium carbonate solution (5 wt % sodium carbonate solution prepared by dissolving 500 mg of Na$_2$CO$_3$ in 9.5 g DI water) was added to increase the pH to ca. 9. The now basic mixture was filtered and rinsed with 50 ml DI water. The yield was 140 mg of chitosan-PGMA. One hundred mg of this intermediate was suspended in 10 ml pH 8.0 borate buffer. 0.148 g (0 9 mmol) of 1,1'-carbonyldiimidazole was added to the suspension and allowed to stir for 2 hours before adding 1.56 g (4.5 mmol) of β-D-lactose. The final mixture was allowed to stir for two days at room temperature. The final solution was filtered through a medium frit, rinsed with 100 ml DI water.

Example 8

Synthesis of Lactose-[branching]-Sand

The synthesis will follow these steps: Five grams of fine sand will be vigorously stirred with 20 ml DI water, then filtered through a medium frit. They will then be mixed with 10 ml pH 8.5 20 mM borate buffer and allowed to stir for few minutes at room temperature. Sixteen mg of 1,1'-carbonyldiimidazole (0.1 mmol, MW 162.15) will then be added to the suspension and allowed to stir for 2 more hours before adding branched poly(ethylene glycol) (2.28 mmol.eq. OH). After two additional hours, 0.37 g (2.28 mmol) of 1,1'-carbonyldiimidazole will be added to the suspension and allowed to stir for 2 more hours before adding 3.9 g (11 4 mmol) of β-D-lactose. Five ml of the pH 8.5 borate buffer will then be added. The final mixture will be allowed to stir for two days at room temperature. The final solution will be filtered through a medium frit and rinsed with 50 ml DI water. The wetness of the solid will be preserved.

Example 9

Synthesis of Lactose-[branching]-Sepharose

The synthesis will follow these steps: One gram of wet Sepharose (ca. 5 wt % in water) will be mixed with 10 ml pH 8.5 20 mM borate buffer and allowed to stir for few minutes at room temperature. Thirty two mg of 1,1'-carbonyldiimidazole (0.2 mmol, MW 162.15) will then be added to the suspension and allowed to stir for 2 more hours before adding branched poly(ethylene glycol) (4.56 mmol.eq. OH). After two additional hours, 0.74 g (4.56 mmol) of 1,1'-carbonyldiimidazole will be added to the suspension and allowed to stir for 2 hours before adding 7.8 g (22.8 mmol) of β-D-lactose. Additional 5 ml of the pH 8.5 buffer will be added. The final mixture will be allowed to stir for two days at room temperature. Fifty ml DI water will be added to the final solution to ensure dissolution of all free reagents. The final solution will be filtered through a medium frit and rinsed with 50 ml DI water. The wetness of the solid will be preserved.

Example 10

Synthesis of Lactose-[branching]-PGMA

The synthesis, including a branched polymer, will follow these steps: One hundred mg of PGMA-NH$_2$ (0.4 mmol equivalents of the repeat unit) will be mixed with 50 ml pH 8.5 20 mM borate buffer and allowed to stir for few minutes at room temperature. Sixty four mg of 1,1'-carbonyldiimidazole (0.4 mmol, MW 162.15) will then be added to the suspension and allowed to stir for 2 hours before adding branched poly(ethylene glycol) (9.12 mmol.eq.OH). After two additional hours, 1.48 g (9.12 mmol) of 1,1'-carbonyldiimidazole will be added to the suspension and allowed to stir for 2 more hours before adding 15.6 g (45 6 mmol) of β-D-lactose. The final mixture will be allowed to stir for two days at room temperature. Fifty ml DI water will be added to the final solution to ensure dissolution of all free reagents. The final solution will be filtered through a medium frit and rinsed with 50 ml DI water. The wetness of the solid will be preserved.

Example 11

Influenza-A Virus

Figure 7:
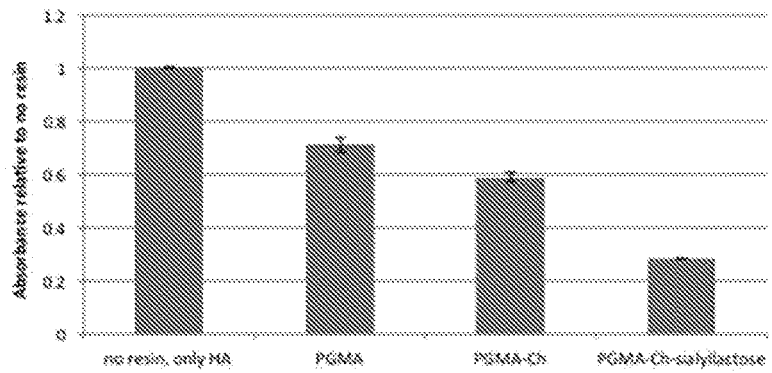

Since influenza's envelope protein, hemagglutinin (HA), is known to strongly bind to innate sialic acid in membranes of host cells, covalently attaching sialyllactose onto insoluble supports would allow virus adsorption to these surfaces. Thus, sialyllactose-complexed with PGMA was prepared following FIG. 5C, 2 using 6'-sialyllactose instead of β-D-lactose as the starting material. The linker therein was chitosan. Chemical derivatization of the material was monitored by recombinant HA binding assays (quantified by the Bradford test) (FIG. 7).

Figure 8:
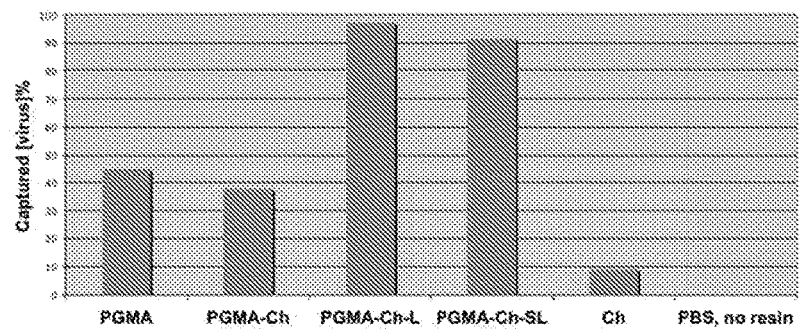
Figure 9:
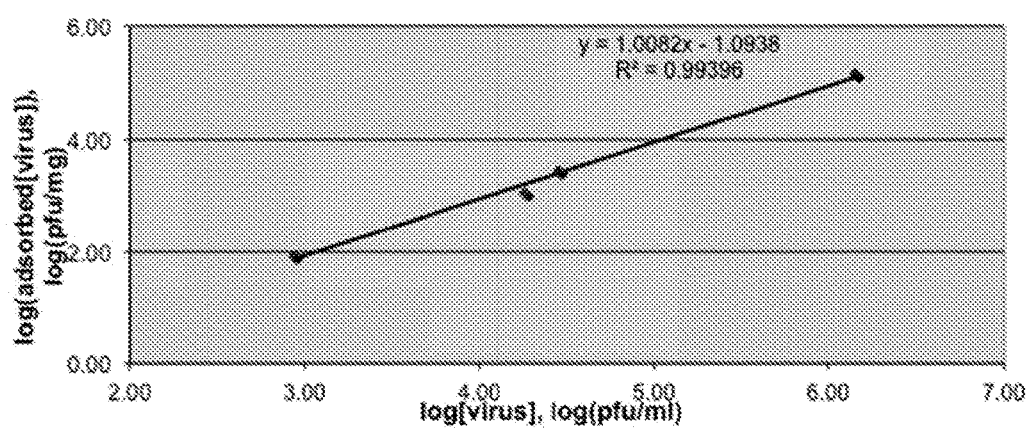

The PGMA-attached sialyllactose along with a set of controls were tested in a buffered (PBS) aqueous solution of PR8 strain of influenza-A virus, with the viral titers in the supernatants quantified using the plaque assay. The results revealed that PGMA-chitosan-lactose removed more than 98% of the virus from solution (Table 1 and FIG. 8). Furthermore, data showed that the virus adsorption to the disclosed material complexes follows a linear isotherm; the relatively constant percentage of adsorbed influenza A to the material complexes reflects Freundlich isotherm that describes adsorption of entities on suspended surfaces at very low surface coverage. Indeed, the linearity between log (adsorbed virus) and log (initial virus) was confirmed by obtaining a $R^2$ coefficient=0.994 (Table 2 and FIG. 9).

TABLE 1

Quantification of influenza A attachment to insoluble materials

| Material | Average # of virus in supernatant ($\times 10^3$ pfu/ml) | Standard Deviation | Captured [virus] % compared to PBS |
| --- | --- | --- | --- |
| PGMA | 7.7 | 1.1 | 45 |
| PGMA-Ch | 8.7 | 2.3 | 38 |
| PGMA-Ch-L | 0.4 | 0.2 | 97 |
| PGMA-Ch-SL | 1.2 | 0.2 | 91 |
| Ch | 12.7 | 2.1 | 9 |
| PBS, no material | 14 | 0.8 | 0 |

PGMA = poly(glycidyl methacrylate),
Ch = chitosan,
SL = sialyllactose,
L = lactose

TABLE 2

Activity of complexed poly(glycidyl methacrylate) polymer while varying the initial titer of influenza A

| Starting [Virus] (pfu/ml) | Adsorbed [Virus] (pfu/mg) | % Adsorbed [virus] |
| --- | --- | --- |
| 1,433,333 | 142133 | 99.2 |
| 28,333 | 2791 | 98.5 |
| 863 | 85 | 98.8 |
| 18000 | 1100 | 93.9 |

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

The invention claimed is:

1. A method for immobilizing a biological comprising:
mixing a fluid sample comprising the biological through a material complex comprising at least one of a hydroxyl-, amino-, mercapto or epoxy-containing material that is fluid-insoluble and at least one receptor selected from lactose, lactose derivative, mono- or poly-saccharide, heparin, chitosan, or any combination thereof, wherein the receptor is bound to the material; and
separating the biological from the sample by adsorbing the biological to the material complex,
wherein the receptor is bound to the material via a linker,
wherein the linker is a repetitively branched molecule, and
wherein said repetitively branched molecule is any of a branched poly(ethylene glycol) (PEG) and a branched poly(ethylenimine) (PEI) or a combination thereof.

2. The method of claim 1, wherein the biological is selected from the group consisting of cell, tissue, tissue product, blood, blood product, body fluid, product of body fluid, protein, vaccine, antigen, antitoxin, biological medicine, biological treatment, virus, microorganism, fungus, yeast, alga, bacterium, prokaryote, eukaryote, *Staphylococcus aureus, Streptococcus, Escherichia coli* (*E. coli*), *Pseudomonas aeruginosa, mycobacterium, adenovirus, rhinovirus,* smallpox virus, influenza virus, herpes virus, human immunodeficiency virus (HIV), rabies, chikungunya, severe acute respiratory syndrome (SARS), polio, malaria, dengue fever, tuberculosis, meningitis, typhoid fever, yellow fever, ebola, shigella, listeria, yersinia, West Nile virus, protozoa, fungi, *Salmonella enterica, Candida albicans, Trichophyton mentagrophytes,* poliovirus, *Enterobacter aerogenes,* Salmonella typhi, Klebsiella pneumonia, *Aspergillus brasiliensis,* and methicillin resistant *Staphylococcus aureus* (MRSA), or any combination thereof.

3. The method of claim 1, wherein the material is selected from the group consisting of agarose, sand, textiles, metallic particles (including nanoparticles), magnetic particles (including nanoparticles), glass, fiberglass, silica, wood, fiber, plastic, rubber, ceramic, porcelain, stone, marble, cement, biological polymers, natural polymers, and synthetic polymers, or any combination thereof.

4. The method of claim 1, wherein the inter-bonding between any combination of receptor, material and the linker is achieved using chemical coupling reagents or physical non-chemical attachment, or a combination of chemical and physical attachments.

5. The method of claim 4, wherein the coupling reagents are selected from 1,1'-carbonyldiimidazole (CDI), N,N'-Dicyclohexylcarbodiimide (DCC), and N-(3-Dimethylaminopropyl)-N'-ethylcarbodiimide hydrochloride (EDC or EDCI), or any combination thereof, and wherein the physical non-chemical attachment is achieved by deposition of receptor molecule, linker molecule, or combination thereof, onto the material.

6. The method of claim 1, wherein the material is chemically functional and the chemical functionality is amino, ammonium, hydroxyl, mercapto, sulfone, sulfinic acid, sulfonic acid, thiocyanate, thione, thial, carboxyl, halocarboxy, halo, imido, anhydrido, alkenyl, alkynyl, phenyl, benzyl, carbonyl, formyl, haloformyl, carbonato, ester, alkoxy, phenoxy, hydroperoxy, peroxy, ether, glycidyl, epoxy, hemiacetal, hemiketal, acetal, ketal, orthoester, orthocarbonate ester, amido, imino, imido, azido, azo, cyano, nitrato, nitrilo, nitrito, nitro, nitroso, pyridinyl, phosphinyl, phosphonic acid, phosphate, phosphoester, phosphodiester, boronic acid, boronic ester, borinic acid, borinic ester, or any combination thereof.

7. The method of claim 6, wherein the epoxy-containing material is Poly(glycidyl methacrylate) (PGMA) and the amino-containing material is PGMA-NH2.

8. The method of claim 6, wherein the hydroxyl, mercapto, or amino group is formed on the surface by modifying the substrate by a chemical transformation comprising a hydrolysis reaction with acid, base, or a combination thereof.

9. The method of claim 1, further comprising physically separating the immobilized biological from the sample by filtration or decantation, by applying gravity or magnetic forces, or any combination thereof.

10. The method of claim 1, further comprising releasing the immobilized biological from the material complex by temperature or irradiation or mechanical or thermodynamic or thermomechanic variations, or any combination thereof; or wherein the immobilized biological is released from the material complex by variations in pH values, concentration of chemicals, ions, sodium chloride, or any combination thereof.

11. A method for immobilizing a biological comprising:
mixing a fluid sample comprising the biological through a material complex comprising at least one of a hydroxyl-, amino-, mercapto or epoxy-containing material that is fluid-insoluble and at least one receptor selected from lactose, lactose derivative, mono- or poly-saccharide, heparin, chitosan, or any combination thereof, wherein the receptor is bound to the material; and
separating the biological from the sample by adsorbing the biological to the material complex,
wherein the receptor is bound to the material via a linker,
wherein the linker is a hyperbranched bis-MPA polyester-16-hydroxyl.

* * * * *